United States Patent
Caimi et al.

(10) Patent No.: US 8,247,208 B2
(45) Date of Patent: Aug. 21, 2012

(54) ZYMOMONAS WITH IMPROVED XYLOSE UTILIZATION IN STRESS CONDITIONS

(75) Inventors: Perry G. Caimi, Kennett Square, PA (US); Mark Emptage, Wilmington, DE (US); Xu Li, Newark, DE (US); Paul V. Viitanen, West Chester, PA (US); Yat-Chen Chou, Lakewood, CO (US); Mary Ann Franden, Centennial, CO (US); Min Zhang, Lakewood, CO (US)

(73) Assignees: Alliance for Sustainable Energy LLC; E I du Pont de Nemours and Company, Wilmington, DE (US)

( * ) Notice: Subject to any disclaimer, the term of this patent is extended or adjusted under 35 U.S.C. 154(b) by 439 days.

(21) Appl. No.: 12/641,642

(22) Filed: Dec. 18, 2009

(65) Prior Publication Data

US 2011/0014670 A1   Jan. 20, 2011

Related U.S. Application Data

(60) Provisional application No. 61/139,852, filed on Dec. 22, 2008.

(51) Int. Cl.
  C12N 1/36   (2006.01)
  C12N 1/20   (2006.01)
  C12P 7/06   (2006.01)
(52) U.S. Cl. .................. 435/245; 435/252.1; 435/161
(58) Field of Classification Search .............. 435/245, 435/252.1, 161
See application file for complete search history.

(56) References Cited

U.S. PATENT DOCUMENTS

| | | | |
|---|---|---|---|
| 5,514,583 | A | 5/1996 | Picataggio et al. |
| 5,712,133 | A | 1/1998 | Picataggio et al. |
| 6,566,107 | B1 | 5/2003 | Zhang |
| 7,223,575 | B2 | 5/2007 | Zhang et al. |
| 7,741,084 | B2 | 6/2010 | Viitanen et al. |
| 7,741,119 | B2 | 6/2010 | Viitanen et al. |
| 2009/0203099 | A1 | 8/2009 | Caimi et al. |
| 2009/0221078 | A1 | 9/2009 | Caimi et al. |
| 2009/0246846 | A1 | 10/2009 | Viitanen et al. |
| 2009/0246876 | A1 | 10/2009 | Viitanen et al. |
| 2009/0269797 | A1 | 10/2009 | Chen et al. |

OTHER PUBLICATIONS

Joachimsthal et al., "A mutant of *Zymomonas mobilis* ZM4 capable of ethanol production from glucose in the presence of high acetate concentrations," Biotechnol Lett 20(2):1998.*
Agrawal, "Growth inhibition of *Zymomonas mobilis* ATCC 10988 by ammonium ions," Biotechnol & Bioeng 34:278-281, 1989.*
Lawford, Hugh G. et al., Improving Fermentation Performance of Recombinant *Zymomonas* in Acetic Acid-Containing Media, Applied Biochemistry and Biotechnology, 1998, pp. 161-172, vol. 70-72, Humana Press Inc.
Mohagheghi, Ali et al., Performance of a newly developed integrant of *Zymomonas mobilis* for ethanol production on corn stover hydrolysate, Biotechnology Letters, 2004, pp. 321-325, vol. 26, Kluwer Academic Publishers.

* cited by examiner

*Primary Examiner* — Rosanne Kosson

(57) ABSTRACT

Strains of xylose utilizing *Zymomonas* with improved xylose utilization and ethanol production during fermentation in stress conditions were obtained using an adaptation method. The adaptation involved continuously growing xylose utilizing *Zymomonas* in media containing high sugars, acetic acid, ammonia, and ethanol.

5 Claims, No Drawings

ZYMOMONAS WITH IMPROVED XYLOSE UTILIZATION IN STRESS CONDITIONS

This application claims the benefit of U.S. Provisional Application 61/139,852, filed Dec. 22, 2008 and is incorporated by reference in its entirety.

STATEMENT OF GOVERNMENT RIGHTS

This invention was made with United States Government support under Contract No. 04-03-CA-70224 awarded by the Department of Energy and Contract No. DE-AC36-08GO28308 between the United States Department of Energy and the Alliance for Sustainable Energy, LLC, the Manager and Operator of the National Renewable Energy Laboratory. The U.S. Government has certain rights in this invention.

FIELD OF INVENTION

The invention relates to the fields of microbiology and fermentation. More specifically, development of Zymomonas strains with improved xylose utilization under stress fermentation conditions is described.

BACKGROUND OF INVENTION

Production of ethanol by microorganisms provides an alternative energy source to fossil fuels and is therefore an important area of current research. It is desirable that microorganisms producing ethanol, as well as other useful products, be capable of using xylose as a carbon source since xylose is the major pentose in hydrolyzed lignocellulosic materials, and therefore can provide an abundantly available, low cost carbon substrate. Zymomonas mobilis and other bacterial ethanologens which do not naturally utilize xylose may be genetically engineered for xylose utilization by introduction of genes encoding 1) xylose isomerase, which catalyses the conversion of xylose to xylulose; 2) xylulokinase, which phosphorylates xylulose to form xylulose 5-phosphate; 3) transketolase; and 4) transaldolase.

There has been success in engineering Z. mobilis cells for xylose metabolism (U.S. Pat. Nos. 5,514,583, 5,712,133, 6,566,107, WO 95/28476, Feldmann et al. (1992) Appl Microbiol Biotechnol 38: 354-361, Zhang et al. (1995) Science 267:240-243), as well as a Zymobacter palmae strain (Yanase et al. (2007) Appl. Environ. Mirobiol. 73:2592-2599). However, typically the engineered strains do not grow and produce ethanol as well on xylose as on glucose. Strains engineered for xylose utilization have been adapted by serial passage on xylose medium, resulting in strains with improved xylose utilization as described in United States Patent Application 20030162271 and commonly owned and co-pending US Patent Application Publication No. US 2008-0286870 A1. It has been shown that these improvements were the result of selection for altered sequences for improved expression of the pGAP promoter regulating expression of the xylose isomerase gene. Those sequences and methods for their use in improved expression of transgenes in Z. mobilis are disclosed in commonly owned and co-pending United States Patent Application Publication Nos. US2009-0246876 A1 and US2009-0246846 A1.

It is desired to use cellulosic hydrolysates as a renewable source of sugars for fermentation media for production of ethanol by biocatalysts. Cellulosic hydrolysates, which are generally produced from biomass by pretreatment and saccharification, typically contain substances that are detrimental to biocatalyst growth and production. For example, acetate is a common product present in cellulosic hydrolysates which has been shown to be inhibitory to Z. mobilis at concentrations routinely found in hydrolysate (Ranatunga et al. (1997) Applied Biochemistry and Biotechnology 67:185-198).

There remains a need for strains of Zymomonas, and other bacterial ethanologens, which have maximized xylose utilization in the presence of stresses imposed by impure sugar sources produced through saccharification of biomass.

SUMMARY OF INVENTION

The invention provides a method for obtaining xylose-utilizing Zymomonas strains that have improved xylose utilization under stress fermentation conditions as well as strains of Zymomonas produced using this method.

Accordingly, the invention provides a method for producing an improved xylose-utilizing Zymomonas strain comprising:
a) providing one or more xylose-utilizing Zymomonas cells;
b) continuously growing the xylose-utilizing Zymomonas cells of (a) in a feeding growth medium comprising at least about 50 g/L xylose whereby a culture comprising ethanol is produced;
c) adding to the culture of (b) an amount of ammonia and acetic acid or ammonium acetate whereby a stress culture comprising ethanol and ammonium acetate is produced;
d) continuously growing the stress culture of (c) whereby improved xylose-utilizing Zymomonas cells are produced; and
e) isolating one or more cells from the culture of (d) wherein at least one or more isolated cells exhibits improved utilization of xylose in the presence of ammonium acetate and ethanol as compared to the xylose-utilizing Zymomonas cells provided in (a), and the improved cell is grown as a strain.

In another embodiment the invention provides improved xylose-utilizing Zymomonas cells and strains obtained using the methods disclosed herein.

In a further embodiment the invention is a stress fermentation adapted xylose-utilizing Zymomonas strain that uses at least about 40%, 45%, 50%, 55%, 60%, 65%, or 70% of available xylose in a mixed sugars medium, e.g. a medium containing 60 g/L xylose, 80 g/L glucose, 9.54 g/L acetate, with pH adjusted to 5.8, when starting at a cell density of 0.1 OD at 600 nm, and under conditions where the corresponding non-adapted strain utilizes about 5%, 10%, 15%, 20%, 25%, or up to about 30% of available xylose.

In a further embodiment, the invention provides a method of producing ethanol comprising:
a) providing an improved stress fermentation adapted xylose-utilizing Zymomonas strain;
b) contacting the strain of a) with a fermentation medium under suitable fermentation conditions wherein ethanol is produced; and
c) optionally isolating the ethanol.

The stress fermentation adapted cells or strains may be provided by the adaptation procedures herein, specifically with reference to adaptation to medium comprising ethanol and ammonium acetate.

DETAILED DESCRIPTION OF THE INVENTION

The present invention describes a method for producing and isolating Zymomonas cells (grown to be strains) that have improved utilization of xylose under stress fermentation conditions. The *Zymomonas* cells to which the method is applied are xylose-utilizing cells, which, according to the invention, are continuously grown under conditions of ammonium acetate and ethanol stress to produce stress fermentation adapted xylose-utilizing *Zymomonas* strains. The present invention is also directed to stress fermentation adapted xylose-utilizing *Zymomonas* strains that are isolated using the present method, and which utilize a higher percent of input xylose under stress fermentation conditions as compared to the cells of the same strain prior to the continuous growth process. The stress fermentation adapted strains may be used in a process for producing ethanol by fermenting sugars. Ethanol produced by the present stress fermentation adapted *Zymomonas* strains may be used as an alternative energy source to fossil fuels.

The following abbreviations and definitions will be used for the interpretation of the specification and the claims.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As used herein "continuously growing" refers to growing with input of new medium and exit flow of effluent such that cells may continue to grow and produce product.

As used herein "stress culture" refers to a culture that includes substances in the medium that cause stress to a biocatalyst used in the culture. Stress of a biocatalyst may be recognized as reduced growth rate, reduced product production, reduced carbohydrate utilization, or other difficulty as compared to function of a biocatalyst used in fermentation without the substances causing stress. Of particular interest are stressers to *Zymomonas* strains that affect sugar utilization for ethanol production. Such stressers include the presence of acetate, ammonia, and ethanol. Of further interest is the effect such stressers have on xylose utilization for the production of ethanol.

As used herein "xylose-utilizing *Zymomona* cell(s)" refers to a cell or cells of a strain that are genetically engineered to express enzymes conferring the ability to use xylose as a carbohydrate source for fermentation.

As used herein "corresponding non-adapted strain" refers to the original xylose-utilizing *Zymomonas* strain that is a strain from which improved strains are produced using the stress adaptation process disclosed herein.

As used herein "feeding growth medium" refers to the medium that is added into the continuous culture vessel.

As used herein "hydrolysate of biomass" and "cellulosic hydrolysate" refer to a product produced from biomass, which is cellulosic material, typically through pretreatment and saccharification processes. Fermentable sugars are present in the hydrolysate, as well as other products.

Increased Xylose Utilization

Applicants have found that xylose-utilizing *Zymomonas* strains may be made to utilize increased amounts of xylose under stress fermentation conditions by adapting the strains through a process involving continuous growth under stress conditions. Increase in xylose utilization is compared to xylose utilization by a xylose-utilizing *Zymomonas* strain that has not undergone adaptation processes as described herein. Stress conditions used herein during adaptation of *Zymomonas* strains provide similar stress conditions to those present when growing *Zymomonas* strains in medium comprising hydrolysate of biomass. Thus the present adapted strains may have increased xylose utilization when grown in medium comprising hydrolysate of biomass, thereby providing more efficient growth and product formation.

Any strain of *Zymomonas* that is able to utilize xylose as a carbon source may be an original or starting strain provided for adaption and used in the present method for preparing the stress fermentation adapted xylose-utilizing *Zymomonas* strains that exhibit the improved xylose utilization in accordance with the present invention. Strains of *Zymomonas*, such as *Z. mobilis*, that have been engineered for xylose fermentation to ethanol are particularly useful. Endogenous genes may provide part of the metabolic pathway, or may be altered by any known genetic manipulation technique to provide a protein with enzyme activity useful for xylose metabolism. For example, the endogenous transketolase may complement other introduced enzyme activities in creating a xylose utilization pathway. Typically four genes may be introduced into a *Zymomonas* strain, such as *Z. mobilis*, for expression of four enzymes involved in xylose metabolism as described in U.S. Pat. No. 5,514,583, which is herein incorporated by reference. These include genes encoding xylose isomerase, which catalyzes the conversion of xylose to xylulose and xylulokinase, which phosphorylates xylulose to form xylulose 5-phosphate. In addition, transketolase and transaldolase, two enzymes of the pentose phosphate pathway, convert xylulose 5-phosphate to intermediates that couple pentose metabolism to the glycolytic Entner-Douderoff pathway permitting the metabolism of xylose to ethanol. DNA sequences encoding these enzymes may be obtained from any of numerous microorganisms that are able to metabolize xylose, such as enteric bacteria, and some yeasts and fungi. Sources for the coding regions include *Xanthomonas, Klebsiella, Escherichia, Rhodobacter, Flavobacterium, Acetobacter, Gluconobacter, Rhizobium, Agrobacterium, Salmonella, Pseudomonads*, and *Zymomonas*. Particularly useful are the coding regions of *E. coli*.

The encoding DNA sequences are operably linked to promoters that are expressed in *Z. mobilis* cells such as the promoters of *Z. mobilis* glyceraldehyde-3-phosphate dehydrogenase (GAP promoter), and *Z. mobilis* enolase (ENO promoter). The coding regions may individually be expressed from promoters, or two or more coding regions may be joined in an operon with expression from the same promoter. The resulting chimeric genes may be introduced into *Zymomonas* and maintained on a plasmid, or integrated into the genome using, for example, homologous recombination, site-directed integration, or random integration. Xylose-utilizing strains that are of particular use include ZM4(pZB5) (described in U.S. Pat. Nos. 5,514,583 , 6,566,107, and U.S. 55,712,133, and incorporated by reference herein), 8b (US 20030162271; Mohagheghi et al., (2004) Biotechnol. Lett. 25; 321-325), as well as ZW658 (ATTCC # PTA-7858), ZW800, ZW801-4, ZW801-5, and ZW801-6 (described in commonly owned and co-pending US Patent Application Publication #US 2008-0286870 A1, which is herein incorporated by reference).

Zymomonas strains that are additionally engineered to utilize other sugars that are not natural substrates, may also be used in the present process. An example is a strain of Z. mobilis engineered for arabinose utilization as described in U.S. Pat. No. 5,843,760, which is herein incorporated by reference.

Adaptation Method

In the present method, a xylose-utilizing strain of Zymomonas (a starting or original strain as described above) is continuously grown in medium comprising xylose under stress fermentation conditions. The medium may contain xylose as the only sugar, or it may contain a mixture of xylose and other sugars such as glucose. Preferred is a high sugars concentration in the medium, for example at least about 50 g/L each of xylose and glucose. There may be more of either or both sugars.

The original xylose-utilizing strain of Zymomonas is first grown continuously without stress conditions and ethanol is produced. Feeding growth medium is added at a dilution rate to maintain the continuous culture. Typically the culture is allowed to stabilize, which may take about 9-12 days, although some cultures may take longer to stabilize. Stabilization is with respect to OD600, sugar utilization, and ethanol production as measured in the effluent from the fermentor. Ethanol in the stabilized culture may be produced to a level of about 18 g/L, 22 g/L, 40 g/L or higher. Additional components are then added to the fermentation medium that cause stress conditions for metabolism of the Zymomonas cells. These components may be added just after stabilization of the culture, or after the culture is fermented under stable conditions for a further period of time. The components that may be added as stressers include ammonia and acetic acid, which results in medium containing ammonium acetate, or ammonium acetate. The presence of ammonium acetate and ethanol in the fermentation medium applies stress to the Zymomonas cells, which typically causes a decrease in OD600, decrease in xylose utilization, and decrease in ethanol production. The dilution rate may be increased or decreased to manage the OD600, xylose utilization, and ethanol concentration. The culture under stress conditions is continuously grown. More ammonia and acetic acid or ammonium acetate may be added at least one or more times during the continuous fermentation of the stress culture. Addition may be more than one time; such as in stages to gradually increase the ammonium acetate concentration in the fermentation medium.

The ammonia and acetic acid may be added as ammonium acetate initially to achieve concentrations of about 24 mM ammonium acetate or about 48 mM ammonium acetate. Ammonia and acetic acid or ammonium acetate may be added in one or more increments to reach concentrations that are between about 64 mM to 210 mM of ammonium acetate. Typically, ammonia and acetic acid or ammonium acetate are added in four or more steps over time to gradually increase the concentration in the fermentation medium of the stress culture. Ethanol in the stress culture is produced by the Zymomonas cells and may vary depending on the production rate, typically ethanol is between about 13 g/L and 54 g/L. The OD600 may vary, and is typically between about 1.5 and about 4.8.

Following a total continuous fermentation period of about two months or more, strains of adapted Zymomonas may be isolated from the stress culture. Samples may be taken from the culture and streaked onto plates to isolate colonies, or grown in culture and then streaked onto plates to isolate colonies. Cells from individual colonies are tested for the capability of isolated cells or strains grown from the cells to utilize xylose and produce ethanol in medium containing high sugar concentration, ammonia and acetate. Ethanol is produced in the cultures by the adapted Zymomonas cells. Among the isolated strains tested, strains are identified that show increased xylose utilization and increased ethanol production as compared to the original or starting xylose-utilizing strain prior to adaptation. One skilled in the art is well aware that there will be variation in the amount of xylose utilized and ethanol produced in different isolated strains. However, strains that have increased xylose utilization and ethanol production will be readily identifiable and recognized among isolates from the stress fermentation cultures.

Adapted Strains

Disclosed herein are stress fermentation adapted xylose-utilizing Zymomonas strains with improved xylose utilization. These strains may be characterized by an increase in utilization of xylose of at least about 12% as compared to the corresponding but non-adapted strain when grown under stress conditions wherein fermentation medium contains ethanol, ammonium acetate and high sugar concentration. Adapted strains may use at least about 12%, 17%, 20%, 25%, or 30% more xylose. Strains of xylose-utilizing Zymomonas having these characteristics may be routinely isolated using the disclosed method. The amount of xylose utilization will depend upon factors including the original strain, the conditions of fermentation, and the particular adapted strain itself.

Under one set of conditions described in Example 3 herein with media containing 60 g/L xylose, 80 g/L glucose, 9.54 g/L acetate, and 160 mM $NH_4OH$ when starting at a cell density of 0.1 OD at 600 nm, improved adapted strains may use at least about 70%, 80%, 85%, or 89% of xylose while the original strain uses about 17% of xylose. Under varied conditions, adapted strains may use at least about 40%, 45%, 50%, 55%, 60%, 65% or 70% of xylose as compared to 30% or less by strains not adapted by stress fermentation as described herein.

Adapted strains of the invention may be used for fermenting sugars to produce fermentation products such as ethanol. The strains are particularly useful for fermentation in medium containing hydrolysate of biomass which contains components providing stress fermentation conditions. Lignocellulosic biomass is typically subjected to certain processes to produce fermentable sugars. These processes may include pre-processing, pretreatment, and saccharification. Pre-processing is any action that renders the biomass more susceptible to pretreatment. Pretreatment is any processing that renders the biomass more susceptible to saccharification. Saccharification includes any processing that hydrolyzes biomass carbohydrates to fermentable sugars. Fermentable sugars include mono and oligo saccharides that can be utilized by a biocatalyst for fermentation. Any commonly known methodologies may be used for pre-processing and pretreating biomass including no pre-processing and/or no pretreatment. Commonly known saccharification techniques may be employed to produce a hydrolysate for fermentation such that sugars are available for utilization, including enzymatic hydrolysis and/or auto or chemical hydrolysis. For example, biomass may be pretreated and saccharified as described in commonly owned and co-pending US Patent Publication US20070031918A1.

Fermentation for Ethanol Production

For production of ethanol, a Zymomonas strain of the invention is contacted with medium that contains mixed sugars including xylose. When the mixed sugars concentration is high such that growth is inhibited, the medium may include sorbitol, mannitol, or mixtures thereof. Galactitol or ribitol may replace or be combined with sorbitol or mannitol. The *Zymomonas* grows in the medium where fermentation occurs and ethanol is produced. The fermentation is run without supplemented air, oxygen, or other gases (which may include conditions such as anaerobic, microaerobic, or microaerophilic fermentation), for at least about 24 hours, and may be run for 30 or more hours. The timing to reach maximal ethanol production is variable, depending on the fermentation conditions. Typically, if inhibitors are present in the medium, a longer fermentation period is required. The fermentations may be run at temperatures that are between about 30° C. and about 37° C., at a pH of about 4.5 to about 7.5.

The xylose-utilizing *Zymomonas* (such as *Z. mobilis*) may be grown in medium containing mixed sugars including xylose in laboratory scale fermenters, and in scaled-up fermentations where commercial quantities of ethanol are produced. Where commercial production of ethanol is desired, a variety of culture methodologies may be applied for producing ethanol utilizing the adapted strains described herein. For example, large-scale production may be run by both batch and continuous culture methodologies. A classical batch culturing method is a closed system where the composition of the medium is set at the beginning of the culture and not subjected to artificial alterations during the culturing process. Thus, at the beginning of the culturing process the medium is inoculated with the desired organism and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable for growth of the present strains and comprise a typical batch system with the exception that the substrate is added in increments as the culture progresses. Fed-Batch systems are useful when catabolite repression is apt to inhibit the metabolism of the cells and where it is desirable to have limited amounts of substrate in the medium. Measurement of the actual substrate concentration in Fed-Batch systems is difficult and is therefore estimated on the basis of the changes of measurable factors such as pH and the partial pressure of waste gases such as $CO_2$. Batch and Fed-Batch culturing methods are common and well known in the art and examples may be found in Biotechnology: A Textbook of Industrial Microbiology, Crueger, Crueger, and Brock, Second Edition (1989) Sinauer Associates, Inc., Sunderland, Mass., or Deshpande, Mukund V., *Appl. Biochem. Biotechnol.*, 36, 227, (1992), herein incorporated by reference.

Commercial production of ethanol may also be accomplished with a continuous culture. Continuous cultures are open systems where a defined culture medium is added continuously to a bioreactor and an equal amount of conditioned medium is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials as is known to one skilled in the art.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by medium turbidity, is kept constant. Continuous systems strive to maintain steady state growth conditions and thus the cell loss due to medium being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Particularly suitable for ethanol production is a fermentation regime as follows. The desired adapted strain is grown in shake flasks in semi-complex medium at about 30° C. to about 37° C. with shaking at about 150 rpm in orbital shakers and then transferred to a 10 L seed fermentor containing similar medium. The seed culture is grown in the seed fermentor anaerobically until $OD_{600}$ is between 3 and 6, when it is transferred to the production fermentor where the fermentation parameters are optimized for ethanol production. Typical inoculum volumes transferred from the seed tank to the production tank range from about 2% to about 20% v/v. Typical fermentation medium contains minimal medium components such as potassium phosphate (1.0-10.0 g/l), ammonium sulfate (0-2.0 g/l), magnesium sulfate (0-5.0 g/l), a complex nitrogen source such as yeast extract or soy based products (0-10 g/l). A final concentration of about 5 mM sorbitol or mannitol is present in the medium. Mixed sugars including xylose and at least one additional sugar such as glucose (or sucrose), providing a carbon source, are continually added to the fermentation vessel on depletion of the initial batched carbon source (50-200 g/l) to maximize ethanol rate and titer. Carbon source feed rates are adjusted dynamically to ensure that the culture is not accumulating glucose in excess, which could lead to build up of toxic byproducts such as acetic acid. In order to maximize yield of ethanol produced from substrate utilized, biomass growth is restricted by the amount of phosphate that is either batched initially or that is fed during the course of the fermentation. The fermentation is controlled at pH 5.0-6.0 using caustic solution (such as ammonium hydroxide, potassium hydroxide, or sodium hydroxide) and either sulfuric or phosphoric acid. The temperature of the fermentor is controlled at 30° C.-35° C. In order to minimize foaming, antifoam agents (any class—silicone based, organic based etc) are added to the vessel as needed. An antibiotic, for which there is an antibiotic resistant marker in the strain, such as kanamycin, may be used optionally to minimize contamination.

Any set of conditions described above, and additionally variations in these conditions that are well known to one skilled in the art, are suitable conditions for production of ethanol by an adapted xylose-utilizing *Zymomonas* strain of the invention.

Ethanol produced in the fermentation may be recovered using various methods known in the art. As a specific example, bioproduced ethanol may be isolated from the fermentation medium using methods known in the art for ABE fermentations (see for example, Durre, *Appl. Microbiol. Biotechnol.* 49:639-648 (1998), Groot et al., *Process. Biochem.* 27:61-75 (1992), and references therein). For example, solids may be removed from the fermentation medium by centrifugation, filtration, decantation, or the like. Then, the ethanol may be isolated from the fermentation medium using methods such as distillation, azeotropic distillation, liquid-liquid extraction, adsorption, gas stripping, membrane evaporation, or pervaporation.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations is as follows: "hr" means hour(s), "min" means minute(s), "sec" means second(s), "d" means day(s), "L" means liter(s), "ml" means milliliter(s), "µL" means microliter(s), "g" means grams, "µg" means microgram(s), "ng" means nanogram(s), "g/L" means grams per liter, "mM" means millimolar, "µM" means micromolar, "nm" means nanometer(s), "µmol" means micromole(s), "pmol" means picomole(s), "OD600" means optical density measured at 600 nm.

General Methods
HPLC Method

The analysis was done with an Agilent 1100 series HPLC and Agilent ChemStation software for LC 3D. The column was BioRad Aminex HPX-87H (HPLC Organic Analysis Column 125-0140) with BioRad Micro-Guard Cartridge Cation-H (125-0129). The operating conditions were:

Flow 0.6 mL/min
Solvent 0.01 N $H_2SO_4$
Stop Time 25 min
Injection Volume 5 µL
Auto Sampler Temp Control @ 10° C. or 4° C.
Column Temp 55° C.
Detector Refractive Index (40° C.) with External Standard Calibration Curves

EXAMPLES

Example 1

Adaptation of *Zymomonas* to Stress Fermentation

Cultures of *Z. mobilis* strain ZW801-4 were grown under conditions of stress as follows. ZW801-4 is a recombinant xylose-utilizing strain of *Z. mobilis* that was described in commonly owned and co-pending US Patent Application Publication #US 2008-0286870 A1, which is herein incorporated by reference. Strain ZW801-4 was derived from strain ZW800, which was derived from strain ZW658, all as described in U.S. patent application Ser. No. 11/862,566. ZW658 was constructed by integrating two operons, $P_{gap}$xylAB and $P_{gap}$taltkt, containing four xylose-utilizing genes encoding xylose isomerase, xylulokinase, transaldolase and transketolase, into the genome of ZW1 (ATCC #31821) via sequential transposition events, and followed by adaptation on selective media containing xylose. ZW658 was deposited as ATCC #PTA-7858. In ZW658, the gene encoding glucose-fructose oxidoreductase was insertionally-inactivated using host-mediated, double-crossover, homologous recombination and spectinomycin resistance as a selectable marker to create ZW800. The spectinomycin resistance marker, which was bounded by loxP sites, was removed by site specific recombination using Cre recombinase to create ZW801-4.

Continuous cultures of ZW801-4 were run in 250 ml stirred, pH and temperature controlled fermentors (Sixfors; Bottmingen, Switzerland). The basal medium for growth was 5 g/L yeast extract, 15 mM ammonium phosphate, 1 g/L magnesium sulfate, and 10 mM sorbitol. The temperature was controlled at 33° C. and pH was 5.8 for the starting cultures. Four cultures were started: two with basal medium plus 50 g/L each of glucose and xylose (fermentors F1 C and F4B), one with basal medium plus 100 g/L glucose and 80 g/L xylose (fermentor F2B), and one with basal medium plus 50 g/L xylose and later increased to 80 g/l xylose (F6). All cultures were started without added ammonium acetate and at an OD600 of 0.1. The effluent was analyzed for ethanol, xylose, and glucose at times noted below by HPLC as described in General Methods. Basal media with added ammonium acetate was used as the stressing media and the concentration of ammonium acetate above that present in the basal media is used in the description below.

The F6 fermentor was run continuously with a dilution rate of 0.065 $h^{-1}$. At 12 days of culture the effluent stabilized at about 18 g/L ethanol, near complete xylose utilization and OD600 of about 3.8, and remained steady until day 21 while the dilution rate was increased to 0.9 $h^{-1}$. At day 21 ammonium acetate was added to give 24 mM in the basal media plus xylose feed. The exit concentration of xylose increased to 10 g/L, OD600 decreased to 1.5 and the ethanol concentration decreased to 14 g/L. The dilution rate was decreased to 0.045 $h^{-1}$. After the dilution rate decrease, xylose in the effluent dropped to near 0, ethanol increase to 20 g/L and OD600 increased to 2.4. At 30 days the ammonium acetate concentration was increased to 32 mM. Xylose and ethanol concentrations in the effluent remained constant but OD600 decreased to 1.8. At 35 days of culture ammonium acetate concentration was increased to 40 mM. The culture condition was held to day 50 when xylose concentration was increase to 80 g/L. Upon the xylose concentration increase, ethanol concentration increased to 30 g/L+/−4 g/L and the dilution rate was increased to 0.08 $h^{-1}$ to maintain OD600 at 4. The ammonium acetate concentration was increased in two equal steps on day 71 and 78 to give 48 mM ammonium acetate. No change in dilution rate or outlet concentration of xylose and ethanol accompanied the ammonium acetate increases. Ammonium and acetate concentrations were further increased in two equal steps to 64 mM by day 92. Dilution rate and ethanol concentration remained constant but OD600 declined to 1.5 by day 98. The cells became aggregated. The culture was moved to a clean fermentor. The OD600 rose to 3.8. The ammonium acetate concentration was increased in two equal steps to 80 mM by day 104. The residual xylose concentration increased to 3 g/L. The continuous culture was run until day 205 while increasing the ammonium acetate concentration to 160 mM in 10 equal steps to a final concentration of 160 mM. The pH was maintained at 5.8. The OD600 stayed between 1.4 and 4, and the residual xylose concentration varied between 2 and 7 g/L.

The F2B fermentor was difficult to control for 25 days and oscillated between about 3 and 8 OD600, 0 and 30 g/L glucose, 20 and 50 g/L xylose and 22 to 70 g/L ethanol. The glucose oscillation dampened after day 25 and stabilized at 5-6 g/L. That glucose concentration and a dilution rate of 0.04 $h^{-1}$ held until day 40. The culture was moved to a clean fermenter on day 43 and the glucose oscillation returned for 8 days before returning to 4 g/L glucose, 30 g/L+/−3 g/L xylose and 60 g/L ethanol at a dilution rate of 0.065 $h^{-1}$ through 76 days of culture.

Fermentor F1 C stabilized at very low glucose and xylose; 40 g/L ethanol, OD600 of 6 and a dilution rate of 0.07 h$^{-1}$ by 10 days of culture. Ammonium acetate was added to 48 mM. The xylose concentration increased to 6 g/L and dilution rate increased to 0.08 h$^{-1}$. Ammonium acetate was increased to 80 mM in 4 equal steps between day 15 and day 23. The culture was moved to a clean fermenter at days 41 and 69. Dilution rate was maintained at between 0.08 and 0.1 h$^{-1}$ as the ammonium acetate concentration was increased step wise to 160 mM by day 97. During the period of ammonium acetate concentration increases the OD600 was between 3.6 and 5.3, the ethanol concentration between 39 and 45 g/L, and the xylose concentration between 0 and 8 g/L. The ammonium concentration was further increased step wise to 210 mM by addition of ammonium hydroxide to the ammonium acetate containing media with phosphoric acid added to maintain the pH at 5.8 by day 139. During this period the OD600 dropped to about 3.2, the ethanol concentration increased to about 51 g/L, and residual xylose concentration was 2.2 g/L.

Fermentor F4B also started with basal medium and 50 g/L each of glucose and xylose with pH maintained at 5.8. It was stable at 40 g/L ethanol, a dilution rate of 0.1 h$^{-1}$ and very low glucose and xylose by day 9. Ammonium acetate concentration was brought to 48 mM on day 12. Dilution rate was decreased to 0.07 h$^{-1}$ to maintain the OD and sugar utilization and ammonium acetate was increased to 64 mM in two equal steps by day 22. Dilution rate varied as did remaining xylose until day 28. Dilution rate remained constant at 0.082 while ammonium acetate was increased to 96 mM in 4 equal steps by day 43. During that period ethanol concentration increased slightly to about 42 g/L and OD600 decreased from about 4.8 to 3.5. At day 51 the feed was changed to basal media with 80 g/L glucose and 60 g/L xylose with 96 mM ammonium acetate. Ethanol concentration increased to 41 to 51 g/L with some day to day variation. Remaining xylose increased to 16 g/L and dilution rate stabilized at 0.09 h$^{-1}$ and OD600 at about 4.9 by day 70. Ammonium acetate was added to a concentration of 160 mM in 8 equal steps by day 126. Ethanol concentration increased to 63 g/L while dilution rate and OD600 remained constant.

As with fermenter F1C, the ammonium concentration was further increased step wise to 210 mM, with phosphoric acid added to maintain the pH at 5.8, by day 168. The dilution rate was maintained at 0.08 h$^{-1}$. During this period the OD600 varied between 3.7 and 5.6, the ethanol concentration increased to about 63 g/L, and residual xylose concentration was at 18 g/L. The culture was maintained for 8 days in this condition and the pH was then maintained at 5.65 for another 7 days. The OD600 dropped to 3.5 while ethanol and xylose concentrations remained relatively constant.

Example 2

Evaluation of Cultures Derived from the Adaptation Continuous Culture Fermenters Samples of the continuous adaptation cultures were first taken from fermentor F1C at day 74, from fermentor F4B at day 69 and from fermentor F6 at day 78 and at various times after the first samplings. All were preserved at −80° C. and revived in RMG5 media for testing. Seed cultures were grown to 4.5 OD600 in basal media plus 75 g/L glucose and 25 g/L xylose at 33° C.

The basal media for testing was: 5 g/L yeast extract, 15 mM ammonium phosphate dibasic, 1 g/L magnesium sulfate, 10 mM sorbitol, and 4 g/L potassium hydrogen carbonate. Carbon source was 80 g/L glucose and 60 g/L xylose. The media was used as is for low stress controls or with the addition of 80 mM, 120 mM or 160 mM ammonium acetate with pH adjusted to 5.8 with phosphoric acid.

Fermentation volume was 100 ml and fermentations were run at 33° C. with shaking at 120 rpm. Growth was started by addition of cells prepared from the seed growth media to a starting OD600 of 0.1. Cells from the seed growth media were harvested by centrifugation and washed with the test media. Growth was monitored by OD at 600 nm. Ethanol, xylose and glucose were all monitored by HPLC. The ZW801-4 strain used to start the adaptation cultures was used as control.

All three adapted cultures grew and used glucose at the same rate as ZW801-4 on media without added ammonium acetate. At 160 mM ammonium acetate ZW801-4 grew after an extended lag period while all 3 adapted cultures used all of the glucose in 42 hr.

While all cultures used 60 g/L xylose at similar rates in media without added ammonium acetate, the three adapted cultures utilized all xylose in 46 hr in media with 120 mM ammonium acetate but ZW801-4 required 60 hr.

The bulk testing procedure was repeated at further adaptation times of the continuous fermenters.

Example 3

Performance of Isolated Adapted Strains

Single colonies were isolated by plating on glucose containing plates and used to grow purified strains from the adapted cultures at various stages as indicated in Table 1. Single colony derived strains were tested using the media and conditions described for the whole culture tests in 160 mM ammonium acetate Seed cultures were grown in DP1 media described above with 75 g/L glucose and 25 g/L xylose. Mixed sugar test fermentations were started by adding seed culture to an initial OD600 nm of 0.1. The initial pH was 5.8; temperature was 33° C. and the 100 ml culture was stirred at 120 rpm in a shaker incubator.

ZW801-4 was used as the non-adapted culture control in each of a set of fermentations that tested different strains isolated from the continuous adaption cultures. A second strain designated NS1302-2, that was isolated from the F4B fermenter in the initial round of testing and that repeatedly utilized more xylose and produced more ethanol when tested versus the ZW8014 unadapted strain in the presence of high levels of ammonium acetate, was used as a positive control in each of the test fermentation sets.

All strains used all of the glucose in the mixed sugar fermentation by 44 hr but all had varying amounts of xylose remaining, so remaining xylose at 44 hr fermentation was used as a measure of adaptation to the stress conditions. Results are given in Table 1.

TABLE 1

Description of strains isolated from continuous culture adaptations and the amount of xylose remaining when they have fermented a starting media of 80 g/L glucose and 60 g/L xylose plus 160 mM ammonium acetate for 44 hours.

| Fermenter | Strain description: conditions at colony isolation | | g/L xylose remaining |
|---|---|---|---|
| none | Control initial strain | ZW801-4 | 55 |
| F4B | Control isolate | NS1302-2 | 10 |
| F1C | 160 mM ammonium acetate pH 5.8 | NS1368-1 | 24 |
| F1C | 160 mM ammonium acetate pH 5.8 | NS1368-2 | 22 |

TABLE 1-continued

Description of strains isolated from continuous culture adaptations and the amount of xylose remaining when they have fermented a starting media of 80 g/L glucose and 60 g/L xylose plus 160 mM ammonium acetate for 44 hours.

| Fermenter | Strain description: conditions at colony isolation | | g/L xylose remaining |
|---|---|---|---|
| F1C | 160 mM ammonium acetate pH 5.8 | NS1368-3 | 11 |
| F1C | 210 mM ammonium acetate pH 5.8 | NS1369-1 | 13 |
| F1C | 210 mM ammonium acetate pH 5.8 | NS1369-2 | 26 |
| F1C | 210 mM ammonium acetate pH 5.8 | NS1369-3 | 22 |
| F1C | 210 mM ammonium acetate pH 5.8 | NS1370-1 | 4 |
| F1C | 210 mM ammonium acetate pH 5.8 | NS1370-2 | 2 |
| F1C | 210 mM ammonium acetate pH 5.8 | NS1370-3 | 17 |
| none | Control initial strain | ZW801-4 | 55 |
| F4B | Control isolate | NS1302-2 | 10 |
| F1C | 210 mM ammonium acetate pH 5.6 | NS1380-1 | 13 |
| F1C | 210 mM ammonium acetate pH 5.6 | NS1380-2 | 15 |
| F1C | 210 mM ammonium acetate pH 5.6 | NS1380-3 | 24 |
| None | Control initial strain | ZW801-4 | 55 |
| F4B | Control isolate | NS1302-2 | 10 |
| F4B | 144 mM ammonium acetate pH 5.8 | NS1371-1 | 55 |
| F4B | 144 mM ammonium acetate pH 5.8 | NS1371-2 | 13 |
| F4B | 160 mM ammonium acetate pH 5.8 | NS1372-1 | 12 |
| F4B | 160 mM ammonium acetate pH 5.8 | NS1372-2 | 8 |
| F4B | 160 mM ammonium acetate pH 5.8 | NS1372-3 | 10 |
| F4B | 210 mM ammonium acetate pH 5.65 | NS1373-1 | 5 |
| F4B | 210 mM ammonium acetate pH 5.65 | NS1373-4 | 8 |
| F4B | 210 mM ammonium acetate pH 5.65 | NS1373-5 | 4 |
| none | Control initial strain | ZW801-4 | 47 |
| F4B | Control isolate | NS1302-2 | 7 |
| F4B | 210 mM ammonium acetate pH 5.8 | NS1383-1 | 4 |
| F4B | 210 mM ammonium acetate pH 5.8 | NS1383-2 | 17 |
| F4B | 210 mM ammonium acetate pH 5.8 | NS1383-3 | 12 |
| none | Control initial strain | ZW801-4 | 47 |
| F4B | Control isolate | NS1302-2 | 7 |
| F6 | 112 mM ammonium acetate pH 5.8 | NS1375-1 | 16 |
| F6 | 112 mM ammonium acetate pH 5.8 | NS1375-2 | 16 |
| F6 | 112 mM ammonium acetate pH 5.8 | NS1375-3 | 21 |
| F6 | 136 mM ammonium acetate pH 5.8 | NS1382-1 | 19 |
| F6 | 136 mM ammonium acetate pH 5.8 | NS1382-3 | 20 |

Strains NS1369, NS1370, NS1372, NS1373, and NS1375 all left less xylose than ZW801 and performed about as well as the positive control, NS1302. They were chosen for further evaluation in media containing 60% by volume hydrolysate produced from ground corn cob that had been pretreated by a dilute ammonia and heat process then enzymatically hydrolyzed with a mixture of cellulase and hemicellulase enzyme preparations at 25% percent pretreated corn cob solids, pH 5.3 and 48° C. for 96 hr, all as described in commonly owned and co-pending US Patent Publication US20070031918A1, which is herein incorporated by reference. The primary sugar and acetate concentrations in the resulting hydrolysate were:
Glucose: 62.3 g/L
Xylose: 40.2 g/L
Arabinose 5.7 g/L
Cellobiose 9.6 g/L
Acetate 6.4 g/L
The remaining 40% of the test media was made to adjust the final media concentrations to the following:
5 g/L yeast extract
2 g/L potassium hydrogen phosphate
1 g/L magnesium sulfate
100 g/L glucose
80 g/L xylose
7 g/L acetate Fermentations were run at 33° C. with pH controlled at 5.8 by the addition of KOH. The starting inoculation was 0.2 as calculated from the OD of seed inoculum produced in base media with 75 g/L glucose and 25 g/L xylose as described for the test fermentations in defined media above.

All strains including ZW801-4 were capable of using all of the glucose in the media under these conditions. The results in terms of xylose remaining at about the point (43 hr) when all glucose was used, ethanol at that point and then xylose remaining and ethanol produced after the rate of xylose utilization had dropped to zero (67 hr) are given in Table 2 below.

TABLE 2

Xylose remaining and ethanol produced from isolate cultures in g/L.

| Fermentor origin | isolate designation | g/L xylose at 43 h | g/L ethanol at 43 h | g/L xylose at 68 h | g/L ethanol at 68 h | Strain name |
|---|---|---|---|---|---|---|
| none | ZW801-4 | 40.1 | 64.5 | 34.3 | 68.0 | ZW801-4 |
| F4B | NS-1302-2 | 24.9 | 72.7 | 20.3 | 75.2 | ZW699 |
| F1C | NS-1370 | 30.8 | 70.7 | 22.7 | 75.7 | ZW702 |
| F1C | NS-1369 | 42.8 | 62.5 | 33.7 | 67.8 | ZW703 |
| F4B | NS-1372 | 29.2 | 75.3 | 24.3 | 72.0 | ZW704 |
| F4B | NS-1373-1 | 26.3 | 73.9 | 12.4 | 80.5 | ZW705 |
| F4B | NS-1373-5 | 30.9 | 71.2 | 17.7 | 78.0 | ZW706 |
| F6 | NS-1375 | 49.7 | 48.2 | 40.8 | 55.2 | ZW707 |

At 67 hours, all isolates except NS-1375 used more xylose, and all isolates except NS-1375 and NS-1369 produced more ethanol than the starting strain ZW801-4 in the high sugar, high acetate conditions of growth. Strains NS-1302-2, NS-1370, NS-1372, NS-1373-1, and NS-1373-5 each used at least about 10 g/L more xylose than ZW801-4. Strain NS1373-1 was renamed as ZW705 and was tested several times using this same protocol with ZW801-4 as the comparator strain. ZW705 consistently produced more ethanol starting from sugar supplemented corn cob hydrolysate. The primary reason for better ethanol production was more complete utilization of available xylose. ZW705 consistently utilized 99 to 100% of glucose, utilized 87 to 90% of available xylose and produced ethanol titers of 80 to 85 g/L. In the same conditions ZW801-4 utilized about 98% of glucose, from 59 to 70% of xylose and produced ethanol titers of from 66 to 70 g/L.

Example 4

Evaluation of the ZW705 Adapted Strain

Batch cultures of ZW705 and ZW801-4, as the control, were grown in 150 ml stirred, pH and temperature controlled flasks. The starting temperature was 30° C. and varied to 27° C. The pH was maintained at 5.8. The medium was mRM3 which contained 10 g/L yeast extract, 2 g/L KH2PO4, 1 g/L Mg SO4, 1.8 g/L sorbitol. The medium was supplemented with acetate, glucose and xylose as listed in Table 3.

After 65.5 hr the cultures were analyzed for xylose, glucose, and ethanol. The results given in Table 3 show a 28% increase in xylose utilization and 18% increase in ethanol production by the adapted ZW705 strain as compared to the original ZW801-4 strain.

TABLE 3

Glucose and xylose utilization, and ethanol production in best adapted strain and control strain.

| | Strain | |
|---|---|---|
| Component | ZW801-4 | ZW705 |
| initial acetate g/L | 10.67 | 10.63 |
| Initial glucose g/L | 110.03 | 109.7 |
| Initial xylose g/L | 91.83 | 91.64 |

TABLE 3-continued

Glucose and xylose utilization, and ethanol production in best adapted strain and control strain.

| | Strain | |
|---|---|---|
| Component | ZW801-4 | ZW705 |
| Final glucose g/L | 0 | 0 |
| Final xylose g/L | 25.9 | 0.14 |
| Ethanol titer g/L | 77.57 | 91.94 |
| Glucose utilization | 100% | 100% |
| Xylose utilization | 72% | 100% |

What is claimed is:

1. A method for producing an improved xylose-utilizing *Zymomonas* strain comprising:
   a) providing xylose-utilizing *Zymomonas* cells;
   b) continuously growing the xylose-utilizing *Zymomonas* cells of (a) in a feeding growth medium comprising xylose, whereby a culture comprising ethanol is produced;
   c) adding to the culture made in (b) an amount of ammonia and acetic acid or ammonium acetate, whereby a stress culture comprising ethanol and ammonium acetate is produced;
   d) continuously growing the stress culture made in (c), whereby improved xylose-utilizing *Zymomonas* cells are produced, wherein the improvement in the cells is increased conversion of xylose to ethanol in the presence of ammonium acetate compared to the *Zymomonas* cells of (a);
   e) isolating one or more cells from the improved culture made in (d); and
   f) growing the one or more improved cells to make the strain.

2. The method according to claim 1, wherein in (c) the addition results in an ammonium acetate concentration of at least 24 mM.

3. The method according to claim 1, wherein the concentration of ammonium acetate is increased at least one time during step (d).

4. The method of claim 1, wherein the xylose in the medium in part (b) is at a concentration of at least 50 g/l.

5. A method according to claim 1 wherein in (b) the ethanol is at least 18 g/L.

* * * * *